United States Patent [19]
Schüler et al.

[11] Patent Number: 5,883,256
[45] Date of Patent: Mar. 16, 1999

[54] PROCESS FOR REMOVING AROMATIC HETEROCYCLIC COMPOUNDS PRODUCT-CONTAINING SOLUTIONS

[75] Inventors: Eckhard Schüler, Marburg; Karl-Heinz Wenz, Weimar, both of Germany

[73] Assignee: Behringwerke Aktiengesellschaft, Marburg, Germany

[21] Appl. No.: 757,089

[22] Filed: Nov. 26, 1996

[30] Foreign Application Priority Data

Nov. 28, 1995 [DE] Germany .................. 195 44 297.0

[51] Int. Cl.⁶ .................. C07D 219/02; C07D 311/82
[52] U.S. Cl. ............... 546/102; 549/392; 544/37; 546/104
[58] Field of Search .................. 546/102, 104; 544/36, 37; 549/392

[56] References Cited

FOREIGN PATENT DOCUMENTS

| 0 050 061 | 4/1982 | European Pat. Off. . |
|---|---|---|
| 0 366 946 | 5/1990 | European Pat. Off. . |
| 9518665 | 7/1995 | WIPO . |

OTHER PUBLICATIONS

Streitwieser, Jr. et al., "Introduction to Organic Chemistry, 3rd Ed., Chapter 31: Heterocyclic Compounds," MacMillan Publishing Company, pp. 998–999 (1985).

Park, T.H. et al.,: Isolation an fluorometric, high–perform liquid chromatographic determination of tacrine. Analytical Biochemistry vol. 159(2), pp. 358–362, 1986.

Chakrabarty, S.G. et al.: Determination of 8–MethoxyPso-–ralem in Plasma by scanning fluorometry after Hinlager chromatography. Clinical Chemistry vol. 24, pp. 1155–1157, 1978. (See page 31 of CAS Search).

*Primary Examiner*—Alan L. Rotman
*Assistant Examiner*—Charanjit S. Aulakh
*Attorney, Agent, or Firm*—Finnegan, Henderson, Farabow, Garrett & Dunner, L.L.P.

[57] ABSTRACT

A process for removing aromatic heterocyclic compounds from a product-containing solution, in particular a protein solution, by bringing the solution into contact with a support material. The process is preferably carried out following a virus inactivation with acridine or acridine derivatives and makes it possible to remove these virus-inactivating agents from the solution without there being any significant product losses or changes in the biological activity of the solution.

20 Claims, No Drawings

PROCESS FOR REMOVING AROMATIC HETEROCYCLIC COMPOUNDS PRODUCT-CONTAINING SOLUTIONS

The present invention relates to a process for removing aromatic heterocyclic compounds from product-containing solutions.

Aromatic heterocyclic compounds such as acridine or acridine derivatives, for example, have been used for a long time in medicine, for example in wound treatment. In addition, it is known that acridine and acridine derivatives can be used to inactivate enveloped viruses and non-enveloped viruses such as poliovirus. In this connection it is sometimes very important to remove the acridine and acridine derivatives once again, after they have been used for the virus inactivation, so that their concentration in the final product remains toxicologically harmless even in the case of long-term treatment.

A simple process for removing acridines from a solution comprises salting them out. Thus, Rivanol®, for example, has been separated from the product by salting out in a variety of protein purification processes. However, this procedure suffers from a variety of disadvantages in regard to a possible application to plasma proteins: in the first place, some of the protein, and consequently the product, can be coprecipitated, thereby leading to losses in yield. In the second place, the separation of acridine and/or its derivatives in such a procedure is not complete after this one step. However, in the case of a pharmaceutical production process, it should be possible to deplete an added agent once again to such an extent that only a few ppm are still present in unbound form in the product. This is especially important when preparing substances which are to be administered repeatedly within the context of a long-term therapy, for example.

The separation of non-denaturing, amphiphilic substances from plasma protein products by precipitation of the plasma proteins is disclosed in EP-A-0 050 061. However, as described above, a precipitation is often not expedient for obtaining a highly pure product.

A process for removing lipid-soluble process chemicals from a biological material by means of hydrophobic exchange chromatography on a C-6 to C-24 resin is disclosed in European Patent No. 0 366 946.

Consequently, an object of the present invention is to make available a process by which aromatic heterocyclic compounds can be removed from product-containing, in particular protein-containing, solutions without significant changes in the product composition or the structure of the individual components occurring at the same time. In association with this, any biological activity of the solution which is present should to a large extent be conserved.

An additional object is to be seen in designing the process in such a way that aromatic heterocyclic compounds which are bound to the products can also be removed from the solution, or else that the binding of aromatic heterocyclic compounds to the products is prevented or at least retarded.

It has now been found that aromatic heterocyclic compounds can be removed from a product-containing solution by bringing the solution into contact with a support material, it being necessary for the support material to have a high affinity for aromatic heterocyclic compounds and a low affinity for the product. Acridine, hypericin, psoralen, methylene blue and derivatives of these compounds are preferably removed from a product-containing solution. Acridine and/or an acridine derivative is/are particularly preferably removed from the solution.

Examples of acridine derivatives are ethacridine, 9-aminoacridine (=Aminacrine), 3,6-acridinediamine (Proflavine), acrisorcin, acrizan chloride (=phenacridan chloride), acridine orange, quinacrine, Acricid, acridone, 9-acridinecarboxylic acid, acranil (1-[(6-chloro-2-methoxy-9-acrinidyl)amino]-3-(diethyl-amine)-2-propanol dihydrochloride), 3,7-diamino-5-phenylphenazinium chloride (phenosafranin, safranin B extra), phenoxazine, phenothiazine and acriflavine (3,6-diamino-10-methylacridinium chloride), and also their salts, such as chlorides, sulfates and bromides. Preferred acridine derivatives are proflavine and acriflavine.

In the novel process, a protein solution or a peptide solution is particularly preferred as a product-containing solution. Aqueous solutions are likewise preferably employed. The solution can, for example, comprise the following starting materials: blood plasma, blood serum, cryoprecipitate, fibrinogen, thrombin, prothrombin, factor V, factor VII, factor VIII, factor F IX, factor X, factor XII, factor XIII, antithrombin III, albumin, prealbumin, α-globulins, β-globulins, gamma-globulins, immunoglobulin G, immunoglobulin M, immunoglobulin A, immunoglobulin D, immunoglobulin E, fibrinogen, fibronectin, α1-antiplasmin, antitrypsin, plasminogen, plasmin, urokinase, prourokinase, PAI-1, PAI-2, protein C, protein S, protein C inhibitor, lyophilized serum, fraction I, fraction II, fraction III, fraction IV, fraction IV-1, fraction IV-2, fraction IV-3, fraction IV-4, fraction V, fraction VI, retinol-binding protein, transferrin, kininogen, tissue plasminogen activator, kallikrein, thrombomodulin, vitronectin, GC globulin, macroglobulin, leucocyte proteinase inhibitor, growth factors, cell culture supernatants from normal and permanent cells, extracts from normal and permanent cells, whole blood, body fluids, cell suspensions, cell culture supernatants, extracts of hybridomas, extracts of animal and plant tissues, extracts or supernatants of microorganisms, secretions of transgenic cells or animals, culture solutions, extracts or suspensions of plant cells, organ extracts, milk, antigen preparations or vaccines.

Any substance which has a high affinity for aromatic heterocyclic compounds and a low affinity for the product can be used as a support material. In this context, affinity is, in the present case, understood to mean the ability of the support material to retain or bind a substance. High and low affinity, respectively, are consequently understood to mean the abilit of the support material to retain or bind aromatic heterocyclic compounds to a large extent or preferably virtually completely, while only retaining or binding the product to a small extent, or preferably not at all, when the solution is brought into contact with the support material.

Examples of suitable support materials are gel matrices, ion exchange matrices, supports which have been modified in a polar manner and hydrophobically modified supports.

Gel matrices are known from gel chromatography. Their activity is based on their pore structure or pore size. Only molecules of up to a particular size (molecular mass) are able to diffuse into the pores. Larger molecules are not able to penetrate into the pores (exclusion limit of the gel) and are entrained by the solvent.

Examples of gel support materials which may be employed in accordance with the invention are the gels which can be obtained from Pharmacia under the trade names Sephadex® (dextran matrix) and Sepharose (agarose matrix), from Merck under the trade name Fractogel® (vinyl polymer matrix) and from Biosepra under the trade name Hyper D®.

However, the separating efficiency of such gels is generally not very high; that is they do not bind relatively small molecules such as acridine and acridine derivatives very strongly. For example, when chromatographing a Rivanol-containing solution through a gel filtration column packed with a conventional gel, the yellow Rivanol was observed to be smeared over the whole of the column.

For this reason, preference is given, in accordance with the invention, to chemically modified support materials whose affinity depends not only on the molecular mass of the substance to be retained but also on the chemical properties of this substance.

Many substances which can be removed in accordance with the invention also exhibit polar properties in addition to their aromatic, hydrophobic basic structure. Thus, they may still possess charged side groups, for example amino groups, at physiological pH. In the case of proflavine, for example, the two amino groups are 97%-protonated, and consequently charged, at pH 7.0. For this reason, ion exchange supports are suitable for the novel process.

Known support materials from ion exchange chromatography are suitable for use as ion exchange supports. In this context, the support material possesses ionic groups having readily dissociable counter-ions. Ionic substances, such as charged acridine derivatives, are adsorbed by "exchange" with the counter-ion when brought into contact with such a support material.

Known ion exchange support materials are, for example, likewise marketed under the abovementioned trade names Sepharose, Fractogel, Sephadex and Hyper D, with these gels then possessing appropriate charged groups. Owing to the polar properties of many aromatic heterocyclic compounds such as acridine and acridine derivatives, these compounds can also be removed from solutions by means of supports which have been modified in a polar manner. Examples of support materials which are suitable for this purpose are those which are modified with cyano, amino or hydroxyl groups, such as cyanopropyl, aminopropyl, diol, aminoethyl and diethylamino groups.

Known gel support materials which are modified in a polar manner are marketed by Merck (Darmstadt) under the trade names LiChroprep CN®, LiChroprep NH$_2$® and LiChroprep Diol®. These support materials also include mixed polymers such as the product marketed by Biosepra under the tradename SDR Hyper D® gel.

Support materials which are modified in a hydrophobic manner, such as known reversed-phase gel supports, are particularly preferred in accordance with the invention. In this context, support materials are especially preferred which are hydrophobically modified with $C_1$–$C_{24}$ side chains. These side chains can be linear or branched $C_1$–$C_{24}$-alkyl, or $C_3$–$C_{24}$-cycloalkyl side groups or aromatic side groups, for example methyl, ethyl, propyl, iso-propyl, butyl, iso-butyl or tert-butyl, and also linear or branched pentyl, hexyl, heptyl, octyl, decyl, dodecyl, octadecyl, icosanyl, tetracosanyl, phenyl or cyclohexyl. Combinations of these groups, and also substituted groups, such as phenylalanine, are also possible.

In order to keep a loss in the yield of the product as low as possible, hydrophobically modified support materials are preferred which possess short side groups, since these materials have a low affinity for proteins. In this context, short side groups are understood to mean those groups which have from 1 to 5 carbon atoms, in particular $C_1$–$C_5$-alkyl groups. Particular preference is given to silica gels which are hydrophobically modified with ethyl groups.

The following commercial products, for example, come into this category of support materials: LiChroprep RP-2 (from Merck, Darmstadt), silanized silica gel 60 (from Merck, Darmstadt) and TMS-250 (C1-alkylated, end-capped with trimethylsilyl groups; from TosoHaas).

In order to reduce the hydrophilic interaction of the product with the support material, and consequently to reduce losses in yield, it is advantageous, for this purpose, to block the charged groups of the support material, e.g. with dimethylsilyl or trimethylsilyl groups. ODS-Prep (C18, end-capped; from TosoHaas) and Prep C18 (from Waters), for example, come into this group of support materials.

Copolymer support materials, which combine non-polar and ion exchange functions, are also suitable for the present invention, in addition to the support materials and mono-functional groups.

Silica gels and silica gel derivatives are preferably employed as the basis for the support materials. However, polymerized resins, for example based on polystyrene, for example Amberchrom® CG-161, Amberchrom ® CG-300 and Amberchrom® CG-1000 (marketed by TosoHaas under these trade names), also offer advantages with regard to the working pH range within which they can be employed.

In accordance with the invention, the solution can be brought into contact with the support material by means of column chromatography or batch chromatography. Furthermore, the possibility exists of bringing the solution into contact with the support material by filtering it through the support material or by allowing it to flow over the support material. In this context, the solution is allowed to flow through or over a suitable device, for example a membrane, which contains the support material or is coated with it. For example, a membrane is suitable on which the functional group, in particular a hydrophobic or charged group, is immobilized. Preferably, aromatic heterocyclic compounds should be removed from a solution which contains up to 50 mg of these substances per ml. The residual content of aromatic heterocyclic compounds in the solution after the latter has been brought into contact with the support material can then be determined by means of photometry, for example fluorescence photometry. Preferably, the residual content is less than 1 ppm, particularly preferably less than 0.1 ppm.

The residual content of aromatic heterocyclic compounds remaining in the solution after the latter has been brought into contact with the support material is due, inter alia, to the binding of aromatic heterocyclic compounds to the product, in particular to proteins. According to the invention, this residual content can be lowered further by adding an additive to the solution before the latter is brought into contact with the support material, which additive substantially prevents the binding of aromatic heterocyclic compounds to proteins or releases aromatic heterocyclic compounds which have already been bound.

In this context, suitable additives are hydrophobic and amphiphilic substances, such as detergents, which may be added to the solution in a concentration of 0.1–5%, preferably of 0.2–1.5% and very preferably of 0.3–1.2%.

If a virus inactivation by means of acridine or acridine derivatives precedes the removal of aromatic heterocyclic compounds, two possibilities then arise for the additive addition. Either the binding of acridine and acridine derivatives to the proteins is reduced, during the virus inactivation by means of acridine or acridine derivatives, by the hydrophobic domains of the proteins being blocked by the addition of hydrophobic or amphiphilic substances, or the acridine or acridine derivative which has already been bound is displaced, after the virus inactivation, by a hydrophobic substance or by a detergent. The approach of only detaching the protein-bound acridine or acridine derivative from the product after a virus inactivation is particularly interesting if the addition of a specific amphiphilic substance or of a detergent would interfere negatively with the virus inactivation method. In this case, it is only possible to add an additive for the purpose of releasing protein-bound acridine or acridine derivatives after the actual virus inactivation by means of acridine or acridine derivatives.

The additive is preferably removed from the solution at the same time as the aromatic heterocyclic compound. Particular preference is given to the novel process in which the simultaneous removal of acridine and/or acridine derivatives and detergents, e.g. Triton X-100, is effected by means of reversed-phase chromatography, by binding these substances to a silica support material to which $C_1$-to $C_{24}$-side groups are bonded.

Examples of suitable additives are polyvinyl alcohols (PVA), polyvinylpyrrolidones, Tween® 20, Tween® 40, Tween® 60, Tween® 80, Nonidet® P40, polyethylene glycols, deoxycholate, CHAPS, ethoxylated alkylphenol (e.g. Triton® X-100), polyoxyethylene which is partially esterified with fatty acid (e.g. Myrj 45), polyoxyethylene fatty alcohol derivatives (e.g. Brij), dodecyl-N-betaine, palmitoyllysolecithin, dodecyl-β-alanine, N-dodecylaminoethanesulfonic acid, tetradecylammonium bromide, hexadecyltrimethylammonium chloride, dodecylpyrimidinium chloride, ethylene oxide-propylene oxide condensates (Pluronic block copolymers), cetyltrimethylammonium bromide, dodecyltrimethyl-benzylammonium chloride (Triton® K-60), ethoxylated amines (Ethomeen), sulfated ethoxylated alkylphenol (Triton® W-30), sodium cholate, sodium deoxycholate, Igepon A (sodium sulfoethylsulfonate), Igepon T (N-methyl-N-oleylethanolsulfonate) and Nacconol® NR (sodium dodecylbenzenesulfonate).

The chemical designation of the trade mark names employed is listed below, provided it has not already been given above:

Tween® 20: } Poly(oxyethylene)$_n$ sorbitan monolaurate

Tween® 40: } Poly(oxyethylene)$_n$ sorbitan monopalmitate

Tween® 60: } Poly(oxyethylene)$_n$ sorbitan monostearate

Tween® 80: } Poly(oxyethylene)$_n$ sorbitan monooleate

Nonidet® P40: Ethylphenol poly(ethylene)$_n$ glycol ether
CHAPS: 3-[(3-Cholamidopropyl)dimethylammonio]-1-propanesulfonate Triton® X-100: Octylphenol poly(ethylene)$_n$ glycol ether In a further embodiment, the novel process follows a process for inactivating viruses with acridine and/or acridine derivatives. For example, a process for preparing virus-inactivated blood plasma can encompass the addition of acridine and/or acridine derivatives to the blood plasma, an incubation of the acridine and/or acridine derivative with the blood plasma and the removal of the acridine and/or acridine derivatives from the blood plasma, as described above. In this context, the acridine and/or acridine derivatives are preferably added in a quantity of from 10 μg to 10 mg per liter. The incubation can be for 1–6 hours and the entire process is preferably carried out at a temperature of from 2° C. to 50° C., in particular at from 10° C. to 37° C. or 10° C. to 25° C.

In a further embodiment of this invention, an additive is added after the incubation step in the process for virus inactivation, which additive substantially prevents the binding of acridine and acridine derivatives to proteins or releases acridine and acridine derivatives which have already been bound. For this purpose, detergents such as Triton X-100 or Triton X-114 are preferably added at a concentration of up to 1%, preferably 0.2–0.8%, very preferably 0.4%–0.7%. The acridine and/or acridine derivatives, together with the additive, are then preferably separated off in one step through a chromatography column containing a hydrophobic support material, in particular a $C_2$- or $C_{18}$-support material, e.g. a LiChroprep-RP-2 column.

In this embodiment, it is furthermore preferred to treat the virus-inactivated solution with Triton X-100 and to incubate it, for example while stirring, for 5–60 minutes, preferably for 5–30 minutes, and then to remove the acridine and/or acridine derivatives, and also the Triton X-100, using a chromatography column.

The novel process enjoys the advantage that aromatic heterocyclic compounds can be removed from a product-containing solution, in particular a protein solution, without any significant, concomitant change in the composition of the product or change in the biological activity of this solution. Furthermore, the advantage arises from a combination of a process for virus inactivation using acridine and/or acridine derivatives and the novel process for removing these substances from the solution that viruses (e.g. non-enveloped viruses, such as Parvoviruses, or enveloped viruses, such as BVDV viruses) which were not inactivated either in the earlier chromatography of virus-containing material or by acridine and/or acridine derivatives are retained by the support material and consequently removed from the product solution, thereby contributing to the overall depletion of virus in a production process.

An additional advantage arises in the use of $C_2$-hydrophobically modified support materials, since the binding of aromatic heterocyclic compounds from aqueous solution proceeds rapidly and efficiently, virtually no hydrophobic material (e.g. proteins of non-viral origin) is bound and any possible product losses are thereby kept to a minimum. This allows aromatic heterocyclic compounds, for example, to be removed rapidly from virus-containing protein solutions which are characterized by very high protein and activity yields.

The following examples are intended to clarify the present invention. With the exception of the values for the concentrations of acriflavine and proflavine, which are given in % by weight, the concentration values refer to % by vol.

EXAMPLE 1

Removal of 0.001% acriflavine from a factor VIII-containing solution using LiChroprep RP-2

In this example, and in the following examples, the concentration values are, with the exception of the values for the concentrations of acriflavine and proflavine, which are given in per cent by weight, given in per cent by volume, as are, for example, the values for PVA and Triton in Examples 2 and 3.

0.001% acriflavine is admixed with 20 ml of a solution which contains factor F VIII and von Willebrand factor at an $OD_{280-320}$ of 2.5 and a pH of 6.9. The mixture is then pumped through a column which contains 4 ml of LiChroprep RP-2. Only 0.2 ppm of acriflavine are still present in the run through. The acriflavine is determined photometrically at 450 mm.

EXAMPLE 2

Removal of 0.001% acriflavine, in the presence of polyvinyl alcohol or polyvinylpyrrolidone, from a factor VIII-containing solution using LiChroprep RP-2

Acriflavine, up to a final concentration of 0.001%, and polyvinyl alcohol PVA (Hoechst AG) or polyvinylpyrrolidone PVP K60 (BASF), in various concentrations, are admixed with 20 ml of a solution which contains factor VIII and von Willebrand factor at an $OD_{280-320}$ of 2.5 and a pH of 6.9. The mixture is then pumped through a column which contains 4 ml of LiChroprep RP-2. The content of acriflavine in the protein solution is then determined photometrically. As can be seen from Table 1 below, the non-specific binding of acriflavine to the protein can be prevented by both PVA and PVP in a concentration-dependent manner.

TABLE 1

Influence of PVA and PVP on the residual concentration of acriflavine which remains in the product

| Additive | Concentration in the mixture [%] | Residual concentration of acriflavine |
|---|---|---|
| PVA | 0.1% | 0.3 ppm |
| PVA | 1.0% | <0.1 ppm*) |
| PVP | 2.0% | <0.1 ppm*) |

*)0.1 ppm is the limit of photometric detection

EXAMPLE 3

Removal of 0.001% acriflavine from a factor VIII-containing solution after the addition of Triton X-100 and using LiChroprep RP-2

Acriflavine, up to a final concentration of 0.001%, is admixed with 20 ml of a solution which contains factor F VIII and von Willebrand factor at an $OD_{280-320}$ of 2.5 and a pH of 6.9. After an incubation period of 4 hours, Triton X-100 is additionally admixed, in various concentrations, with the mixture and, after having been stirred for 10 minutes, the mixture is pumped through a column which contains 4 ml of LiChroprep RP-2. The content of acriflavine in the protein solution is then determined photometrically. As can be seen from Table 2 below, the acriflavine can be displaced by Triton X-100, in a concentration-dependent manner, from its non-specific binding to the protein.

TABLE 2

Influence of Triton X-100 on the residual concentration of acriflavine which remains in the product

| Additive | Concentration in the mixture [%] | Residual concentration of acriflavine |
|---|---|---|
| Triton X-100 | 0.1% | 0.4 ppm |
| Triton X-100 | 0.2% | 0.2 ppm |
| Triton X-100 | 0.4% | <0.1 ppm*) |
| Triton X-100 | 0.5% | <0.1 ppm*) |

*)0.1 ppm is the limit of photometric detection

We claim:

1. A process for removing an antiviral aromatic heterocyclic compound selected from the group consisting of acridine, hypericin, psoralen, methylene blue and derivatives of these compounds from a product-containing solution, which comprises contacting the solution with a solid support material having a high affinity for the aromatic heterocyclic compound and a low affinity for the product to selectively remove the aromatic heterocyclic compound from the solution, wherein the solution contains an additive which substantially prevents the binding of the aromatic heterocyclic compound to a protein or releases an aromatic heterocyclic compound which has already been bound to a protein.

2. The process as claimed in claim 1, wherein the aromatic heterocyclic compound is acridine and/or an acridine derivative.

3. The process as claimed in claim 1, wherein the product-containing solution is a protein solution.

4. The process as claimed in claim 1, wherein the product-containing solution is an aqueous solution.

5. The process as claimed in claim 1, wherein the solid support material is a gel support, an ion exchange support, a support which has been modified in a polar manner or a hydrophobically modified support.

6. The process as claimed in claim 5, wherein the support material is hydrophobically modified.

7. The process as claimed in claim 6, wherein the support material is hydrophobically modified with $C_1$–$C_{24}$ side groups.

8. The process as claimed in claim 7, wherein the support material is hydrophobically modified with $C_1$–$C_5$ side groups.

9. The process as claimed in claim 1, wherein the support material is a silica gel.

10. The process as claimed in claim 9, wherein the silica gel is hydrophobically modified with ethyl groups.

11. The process as claimed in claim 1, wherein the process is carried out by means of column chromatography or batch chromatography.

12. The process as claimed in claim 1, wherein the process is carried out by filtration through the solid support material or flow over the solid support material.

13. The process as claimed in claim 1, wherein the aromatic heterocyclic compound is removed from the solution apart from a residual content of less than 1 ppm.

14. The process as claimed in claim 1, wherein the additive is a hydrophobic or amphiphilic substance.

15. The process as claimed in claim 14, wherein the additive is selected from the group consisting of a polyvinyl alcohol, a polyvinylpyrrolidone, poly(oxyethylene)$_n$ sorbitan monolaurate, poly(oxyethylene)$_n$ sorbitan monopalmitate, poly(oxyethylene)$_n$ sorbitan monostearate, poly(oxyethylene)$_n$ sorbitan monooleate, ethylphenol poly (ethylene)$_n$ glycol ether, a polyethylene glycol, deoxycholate, 3-{(3-cholamidopropyl)dimethylammonio}-1-propanesulfonate, ethoxylated alkylphenol, polyoxyethylene which is partially esterified with fatty acid, a polyoxyethylene fatty alcohol derivative, dodecyl-N-betaine, palmitoyllysolecithin, dodecyl-β alanine, N-dodecylaminoethanesulfonic acid, tetradecylammonium bromide, hexadecyltrimethylammonium chloride, dodecylpyrimidinium chloride, an ethylene oxide-propylene oxide condensate, cetyltrimethylammonium bromide, dodecyltrimethylbenzylammonium chloride, an ethoxylated amine, sulfated ethoxylated alkylphenol, sodium cholate, sodium deoxycholate, sodium sulfoethylsulfonate, N-methyl-N-oleyl-ethanolsulfonate and sodium dodecylbenzenesulfonate.

16. The process as claimed in claim 14, wherein the additive is a polyvinyl alcohol or polyvinylpyrrolidone, or an ethoxylated alkylphenol.

17. The process as claimed in claim 1, wherein the additive is removed from the solution at the same time as the aromatic heterocyclic compound.

18. A process for preparing a virus-inactivated solution, comprising adding an acridine and/or acridine derivative to the solution, incubating the acridine and/or acridine derivative with the solution, subsequently removing the acridine and/or acridine derivative from the solution in accordance with the process as claimed in claim 1.

19. The process as claimed in claim 18, wherein the solution is blood plasma or a plasma product.

20. The process as claimed in claim 2 wherein the aromatic heterocylic compound is proflavine.

* * * * *

UNITED STATES PATENT AND TRADEMARK OFFICE
CERTIFICATE OF CORRECTION

PATENT NO. : 5,883,256
DATED : March 16, 1999
INVENTOR(S) : Eckhard Schüler et al.

It is certified that error appears in the above-identified patent and that said Letters Patent is hereby corrected as shown below:

On the Title Page, Item [54], in the Title, line 2, after "COMPOUNDS", insert --FROM--.

Column 1, line 2, in the Title, after "COMPOUNDS", insert --FROM--.

Claim 13, Column 8, Line 31, "heterocylic" should read --heterocyclic--.

Claim 15, Column 8, Line 46, "dodecyl-βalanine" should read --dodecyl-β-alanine--.

Claim 17, Column 8, Line 61, "heterocylic" should read --heterocyclic--.

Claim 18, Column 8, Line 65, "after "solution,", insert --and--.

Claim 20, Column 9, Line 3, after "claim 2", insert --,--.

UNITED STATES PATENT AND TRADEMARK OFFICE
CERTIFICATE OF CORRECTION

PATENT NO. : 5,883,256
DATED : March 16, 1999
INVENTOR(S) : Eckhard Schüler et al.

It is certified that error appears in the above-indentified patent and that said Letters Patent is hereby corrected as shown below:

Claim 20, Column 9, Line 4, "heterocylic" should read --heterocyclic--.

Signed and Sealed this

Fifth Day of October, 1999

*Attest:*

Q. TODD DICKINSON

*Attesting Officer*  Acting Commissioner of Patents and Trademarks